(12) United States Patent
Wang et al.

(10) Patent No.: US 10,809,253 B2
(45) Date of Patent: Oct. 20, 2020

(54) ANALYTE DETECTION WITH MAGNETIC SENSORS

(71) Applicants: MagArray, Inc., Milpitas, CA (US); The Board of Trustees of the Leland Stanford Junior University, Stanford, CA (US)

(72) Inventors: Shan Xiang Wang, Palo Alto, CA (US); Sebastian J. Osterfeld, Mountain View, CA (US); Heng Yu, Campbell, CA (US); Nader Pourmand, San Mateo, CA (US); Robert L. White, Palo Alto, CA (US)

(73) Assignees: MagArray, Inc., Milpitas, CA (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/831,219

(22) Filed: Dec. 4, 2017

(65) Prior Publication Data
US 2018/0128822 A1 May 10, 2018

Related U.S. Application Data

(62) Division of application No. 12/234,506, filed on Sep. 19, 2008, now Pat. No. 9,863,939.
(Continued)

(51) Int. Cl.
*G01N 33/543* (2006.01)

(52) U.S. Cl.
CPC ............... *G01N 33/54326* (2013.01); *Y10T 436/143333* (2015.01)

(58) Field of Classification Search
CPC .............. G01N 33/54326; Y10T 436/143333
See application file for complete search history.

(56) References Cited

U.S. PATENT DOCUMENTS 5,981,297 A   11/1999  Baselt
6,323,634 B1  11/2001  Nakagawa et al.
(Continued)

FOREIGN PATENT DOCUMENTS

JP   A-2006-112976   4/2006
JP   A-2009-115590   5/2009
(Continued)

OTHER PUBLICATIONS

Baselt; et al., (1998) "A Biosensor Based on Magnetoresistance Technology," Biosensors and Bioelectronics, 13(7-8): 731-739.
(Continued)

*Primary Examiner* — Rebecca M Fritchman
(74) *Attorney, Agent, or Firm* — Rudy J. Ng; Bret E. Field; Bozicevic, Field & Francis LLP

(57) ABSTRACT

Methods for analyte detection with magnetic sensors are provided. Aspects of the methods include producing a magnetic sensor device having a magnetically labeled analyte from a sample, such as a serum sample, bound to a surface of a magnetic sensor thereof; and obtaining a signal, e.g., a real-time signal, from the magnetic sensor to determine whether the analyte is present in the sample. Also provided are devices, systems and kits that find use in practicing the methods of the invention. The methods, devices, systems and kits of the invention find use in a variety of different applications, including detection of biomarkers, such as disease markers.

32 Claims, 9 Drawing Sheets

Related U.S. Application Data

(60) Provisional application No. 60/973,973, filed on Sep. 20, 2007, provisional application No. 61/086,411, filed on Aug. 5, 2008.

(56) References Cited

U.S. PATENT DOCUMENTS

| | | | |
|---|---|---|---|
| 6,582,921 | B2 | 6/2003 | Mirkin et al. |
| 6,623,983 | B1 | 9/2003 | Terstappen et al. |
| 6,679,130 | B2 | 1/2004 | Hajduk et al. |
| 7,906,345 | B2 | 3/2011 | Wang et al. |
| 9,151,763 | B2 | 10/2015 | Osterfeld |
| 9,164,100 | B2 | 10/2015 | Osterfeld |
| 9,528,995 | B2 | 12/2016 | Osterfeld |
| 9,863,939 | B2 | 1/2018 | Wang et al. |
| 2002/0014408 | A1 | 2/2002 | Schroeder |
| 2002/0060565 | A1* | 5/2002 | Tondra ............. G01N 27/745 324/260 |
| 2003/0204133 | A1 | 10/2003 | Harjunmaa et al. |
| 2004/0002121 | A1 | 1/2004 | Regan et al. |
| 2004/0002169 | A1 | 1/2004 | Kraus et al. |
| 2004/0086424 | A1 | 5/2004 | Schembri |
| 2004/0087008 | A1 | 5/2004 | Schembri |
| 2004/0157271 | A1* | 8/2004 | Kirakossian ....... G01N 33/5091 435/7.2 |
| 2005/0025969 | A1 | 2/2005 | Berning et al. |
| 2005/0100930 | A1 | 5/2005 | Wang et al. |
| 2005/0258821 | A1 | 11/2005 | Wang et al. |
| 2006/0051247 | A1 | 3/2006 | Micklash et al. |
| 2006/0269385 | A1 | 11/2006 | Zobel et al. |
| 2007/0003994 | A1 | 1/2007 | Simpson et al. |
| 2007/0122898 | A1 | 5/2007 | Sharma |
| 2007/0166835 | A1 | 7/2007 | Bobrow et al. |
| 2007/0178504 | A1 | 8/2007 | Colpitts et al. |
| 2007/0237673 | A1 | 10/2007 | Ikeda et al. |
| 2008/0024117 | A1 | 1/2008 | Hong et al. |
| 2008/0039339 | A1* | 2/2008 | Hassibi ............... C12Q 1/6818 506/9 |
| 2008/0160622 | A1 | 7/2008 | Su et al. |
| 2009/0005495 | A1 | 1/2009 | Ban et al. |
| 2009/0104707 | A1 | 4/2009 | Wang et al. |
| 2010/0188075 | A1 | 7/2010 | Litvinov et al. |
| 2011/0027901 | A1 | 2/2011 | Gaster et al. |

FOREIGN PATENT DOCUMENTS

| | | |
|---|---|---|
| WO | 2001014591 | 3/2001 |
| WO | 2001057506 | 8/2001 |
| WO | 2003031977 | 4/2003 |
| WO | 2003054523 | 7/2003 |
| WO | 2003081202 | 10/2003 |
| WO | WO 2005059929 | 6/2005 |
| WO | 2008001261 | 1/2008 |

OTHER PUBLICATIONS

Bozorth, (1951) "Ferromagnetism," D. Van Nostrand Company, Inc. 190-209.
Ferreira; et al., (2003) "Detection of biomolecular recognition using nanometer-sized magnetics labels and spin-valve sensors," Digest of Intermag, IEEE International Magnetics Conference, EC-4, XP010665265, isbn: 0-7803-7647-1.
Ferreira; et al., (2003) Biodetection using magnetically labeled biomolecules and arrays of spin valve sensors (invited), Journal of Applied Physics, 93(10): 7281-7286, XP012058127, ISSN: 0021-8979.
Freitas; et al., (2003) "Magnetoresistive biochips," Europhysics News, 34(6): 224-226, XP002429397, ISSN: 0531-7479.
Graham; et al., (2002) "Single Magnetic Microsphere Placement and Detection on-chip Using Current Line Designs with Integrated Spin Valve Sensors: Biotechnological Applications," J. Appl. Phys., 91: 7786-7788.
Graham; et al., (2003) "High sensitivity detection of molecular recognition using magnetically labelled biomolecules and magnetoresistive sensors," Biosensors and Bioelectronics, 18(4): 483-488, XP002429396.
Guanxiong; et al., (2003) "Analytical and micromagnectic modeling for detetion of a single magnetic microbead or nanobead by spin valve sensors," IEE Trans. Magn., 39(5): 3313-3315, XP011101285, ISSN: 0018-9464.
Lagae; et al., (2002) "On-chip manipulation and magnetization assessment of magnetic bead ensembles by integrated spin-valve sensors," J. Appl. Phys., 91(10): 7445-7447, XP012054843, ISSN: 0021-8979.
Li; et al. (2003) "Analytical and Micromagnectic Modeling for Detection of a Single Magnectic Microbead or Nanobead by Spin Valve Sensors," IEEE Tran Magn., 39(5): 33313-3315.
Li; et al., (2003) "Detection of Single Micron-Sized Magnectic Bead and Magnetic Nanoparticles Using Spin Valve Sensors for Biological Applications," J. Appl. Phys., 93(10): 7557-7559.
Miller; et al., (2001) "A DNA Array Sensor Utilizing Magnetic Microbeads and Magnetoelectronic Detection," J. of Magnetism and magnetic Materials, 225: 138-144.
Murray; et al., (2001) "New Aspects of Nanocrystal Research," MRS Bulletin, 26(12): 985-991.
Parkin; et al., (1990) "Oscillations in Exchange Coupling and Magnetoresistance in Mettallic Superlattice Structures: CoJRU, CoICR, and FeICR," Phys. Rev. Lett., 64(19):2304-2307.
Parkin; et al., (1999) "Exchange—Biased Magnetic Tunnel Junctions and Application to Nonvolatile Magnetic Random Access Memory (Invited)," J. Appl. Phys.,85(8): 5828-5833.
Schena; et al., (2000) "Microarray Biochip Technology," Eaton Publishing, 1-18.
Sellmyer; et al., (2002) "Handbook of Thin Film Materials," Edited by: Nalwa, H.S., Stanford Scientific Corporation; Academic Press, 5:337-374.
Slonczewski; (1998) et al., "Micromagnetics of Laminated Permalloy Films," IEEE Tran Magn., 24(3): 2045-2054.
Sun; et al., (1999) "Synthesis of Monodisperse Cobalt Nanocrystals and their Assembly into Magnetic Superlattices," J. Appl. Phys., 85(8) 4325-4330.
Sun; et al., (2002) "Polymer Mediated Self-Assembly of Magnetic Nanoparticles," J. Am. Chem. Soc., 124(12): 2884-2885.
Sun; et al., (2004)"Monodisperse MFe2O4 (M=Fe, Co, Mn) Nanoparticles;" IBM T.J. Watson Research Center, Yorktown Heights, NY, 1-24.
Tehrani; (2000) et al., "Recent Developments in Magnetic Tunnel Junction MRAM," IEE Trans. Magn., 2752-2757.
Thorsen; (2002) et al., "Microlluidic Large-Scale Integration," Science, 298: 580-584.
Trademark Electronic Search System (Tess) for "MAGARRAY;" (2004),3 pages.
Van de Veerdonk, et al., (1997) "Current Distribution Effects in Magnetoresistive Tunnel Junctions;" Appl. Phys. Lett. 71 (19):2839-2841.
Wang; et al., (2003) "Design and fabrication of bio-magnetic sensors and magnetic nanobead labels for dna detection and identification", Digest of Intermag 2003, IEEE International Magnetics Conference, EC-1, XP01066526, ISBN: 0-7803-7647-1.
Han; et al., (2006) "CMOS integrated DNA microarray based on GMR sensors," IEDM '06, 1-4.
Han; et al., (2007) "A High-Density Magnetoresistive Biosensor Array with Drift-Compensation Mechanism," IEEE International Solid-State Circuits Conference, Session, 8: 168-169, 594.
Li; et al., (2006) "Spin valve sensors for ultrasensitive detection of superparamagnetic nanoparticles for biological applications", Sensors and Actuators, 126(1): 98-106.
Xu; et al., (2008) "Giant magnetoresistive biochip for DNA detection and HPV genotyping", Biosensors and Bioelectronics, 24(1): 99-103.

* cited by examiner a Sensor functionalization b Analyte incubation c Linker incubation d Nanotag-based quantificatio

ANALYTE DETECTION WITH MAGNETIC SENSORS

CROSS-REFERENCE TO RELATED APPLICATIONS

This application is a divisional of U.S. application Ser. No. 12/234,506, filed Sep. 19, 2008, now U.S. Pat. No. 9,863,939, which claims the benefit pursuant to 35 U.S.C. § 119(e) of U.S. Provisional Application Ser. No. 60/973,973 filed Sep. 20, 2007 and 61/086,411 filed Aug. 5, 2008; the disclosures of each of which are herein incorporated by reference.

ACKNOWLEDGMENT OF GOVERNMENT SUPPORT

This invention was made with Government support under Grant Nos. 1U54CA119367-01, PO1-HG000205, N43C0-2007-00030, and R43AI072800 awarded by the NIH, DARPA/Navy Grant No. N00014-02-1-0807, and U.S. Department of Defense grant number HDTRA1-07-1-0030-P-1. The Government has certain rights in this invention.

INTRODUCTION

A consensus is emerging that early detection and personalized treatment in clinics based on genetic and proteomic profiles of perhaps 4-20 biomarkers are the key to improving the survival rate of patients with complex diseases such as cancer. While the tools for large scale biomarker discovery with hundreds to thousands of biomarkers are available, there are few biomolecular detection tools capable of multiplex and sensitive detection of biomarkers which can be readily adopted in clinical settings for biomarker validation and for personalized diagnosis and treatment.

SUMMARY

Methods for analyte detection with magnetic sensors are provided. Aspects of the methods include producing a magnetic sensor device having a magnetically labeled analyte from a sample, such as a serum sample, bound to a surface of a magnetic sensor thereof; and obtaining a signal, e.g., a real-time signal, from the magnetic sensor to determine whether the analyte is present in the sample. In certain embodiments, the methods include simultaneously quantifying one or more analytes in the sample. Also provided are devices, systems and kits that find use in practicing the methods of the invention. The methods, devices, systems and kits of the invention find use in a variety of different applications, including detection of biomarkers, such as disease markers.

BRIEF DESCRIPTION OF THE FIGURES

FIG. 7a shows wide sensor vs. narrow sensor geometry. FIG. 7b shows a graph of signal development vs. sensor size.

FIG. 9a shows a schematic of reverse phase protein chip in which analytes are spotted on the chip directly and detection antibodies are then incubated with the spots site-specifically. FIG. 9b shows an image of 64 samples spotted on a magneto-nano chip.

DEFINITIONS

Figure 1:
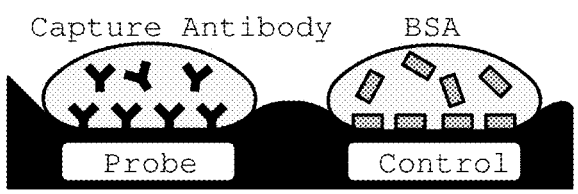
FIG. 1 shows a schematic of a magnetic nanotag-based protein detection assay.
Figure 1:
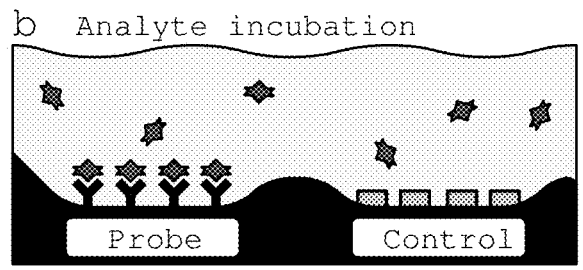
Figure 1:
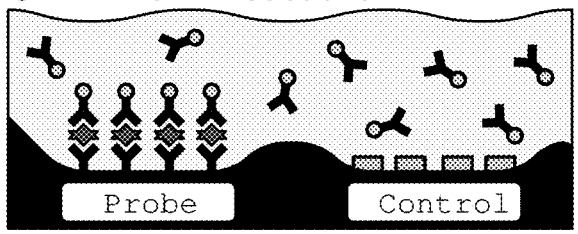
Figure 1:
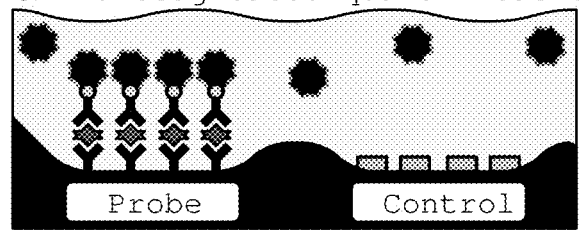

The term "probe," as used herein, refers to a moiety that is complementary to a target analyte of interest. In certain cases, detection of a target analyte requires association of a probe to a target. In certain embodiments, a probe may be immobilized on a surface of a substrate, where the substrate can have a variety of configurations, such as, but not limited to, a sheet, bead, or other structure. In certain embodiments, a probe may be present on a surface of a planar support, e.g. in the form of an array.

An "array," includes any two-dimensional or substantially two-dimensional (as well as a three-dimensional) arrangement of addressable regions, e.g. addressable regions, e.g., spatially addressable regions or optically addressable regions bearing probes, particularly probes that are specific for the target analytes of interest. Where the arrays are arrays of nucleic acids or proteins, the nucleic acids or proteins may be adsorbed, physisorbed, chemisorbed, or covalently attached to the arrays at any point or points along the nucleic acid chain.

An array is "addressable" when it has multiple regions of different moieties (e.g. different probes) such that a region (i.e., a "feature" or "spot" of the array) at a particular predetermined location (i.e., an "address") on the array contains a particular probe. Array features are typically, but need not be, separated by intervening spaces. An array is also "addressable" if the features of the array each have a detectable signature (e.g. a magnetic signature) that identifies the moiety present at that feature.

The term "nucleic acid" as used herein describes a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "biomarker" as used herein refers to an indicator of a particular disease state or a particular state of an organism. In some cases, a biomarker is a characteristic that is measured and evaluated as an indicator of normal biologic processes, pathogenic processes, or pharmacologic responses to a therapeutic intervention. In some cases, a biomarker may be a physiological indicator such as, but not limited to, blood pressure, heart rate or the like. In some cases, a biomarker may be a molecular biomarker, such as but not limited to proteins, nucleic acids, carbohydrates, small molecules, and the like. For instance, examples of molecular biomarkers include, but are not limited to, elevated prostate specific antigen, which may be used as a molecular biomarker for prostate cancer, or using enzyme assays as liver function tests. In certain embodiments, a biomarker may indicate a change in expression or state of a protein that correlates with the risk or progression of a disease, or with the susceptibility of the disease to a given treatment.

In certain cases, the disease may be a proliferative disease. As used herein the term "proliferative disease" refers to a disease characterized by the growth or rapid increase in size or number of tissues or cells. Examples include, but are not limited to, cancers, tumors, papillomas, sarcomas, carcinomas, and the like.

As used herein, the terms "processor", "central processing unit", or "CPU" refer to the part of a computer (i.e., a microprocessor chip) that performs data processing. In certain embodiments, a processor may be under the control of a software program and thus is suitably programmed to execute all of the steps or functions required of it, and may also include any hardware or software combination that will perform such required functions. For example, in some cases, a processor may input data (e.g. a data signal), process the data to obtain a result, and output the result on a computer-readable medium in a user-readable format. In certain embodiments, the processor may be configured to obtain a real-time signal. As used herein, the term "real time" refers to events or signals that are detected or obtained as they happen or as soon as possible after they occur.

DETAILED DESCRIPTION

Methods for analyte detection with magnetic sensors are provided. Aspects of the methods include producing a magnetic sensor device having a magnetically labeled analyte from a sample, such as a serum sample, bound to a surface of a magnetic sensor thereof; and obtaining a signal, e.g., a real-time signal, from the magnetic sensor to determine whether the analyte is present in the sample and, in certain embodiments, to simultaneously quantify one or more analytes in the sample. Also provided are devices, systems and kits that find use in practicing the methods of the invention. The methods, devices, systems and kits of the invention find use in a variety of different applications, including detection of biomarkers, such as disease markers.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing embodiments of the invention, aspects of the methods will be described first in greater detail. Next, embodiments of systems and kits that may be used in practicing methods of invention are reviewed. In addition, a review is provided of embodiments of different applications in which methods, systems and kits of the invention find use.

Methods

As summarized above, embodiments of the invention are directed to methods of determining whether an analyte is present in a sample, i.e., determining the presence or absence of an analyte in a sample, and, in certain embodiments, simultaneously quantifying one or more analytes in the sample. Aspects of the methods include a step of producing a magnetic sensor device having a magnetically labeled analyte bound to a surface of a magnetic sensor thereof. Magnetic sensor devices that find use in methods of the invention are described in greater detail below. The magnetically labeled analyte bound to a surface of a sensor of the device may be produced using a number of different protocols. For example, analyte may first be bound to a specific receptor on the sensor surface, and then subsequently magnetically labeled. Alternatively, sample and magnetic label may be combined prior to contact with the sensor, and the resultant labeled analyte then allowed to bind to the sensor. In yet other embodiments, the sample of interest is first positioned on the sensor, and then contacted with magnetically labeled reagent specific for sample analyte of interest.

In certain embodiments, the methodology employed is one that uses a "real-time" signal. In certain embodiments, the assay of interest is a multiplex protein assay in which a complex sample, such as a serum sample, is assayed to determine whether two or more distinct protein analytes are present in the sample. In this latter type of embodiment, the signal employed may or may not be a real-time signal.

Real-Time Signal

In certain embodiments, the methods disclosed herein employ a "real time" signal. As such, embodiments of the invention including obtaining a real time signal from the device and employing that signal to determine at least the presence or absence of a given analyte of interest in a sample. Accordingly, embodiments of the invention observe the evolution in real time of the signal associated with the presence of the analyte of interest, and indeed of multiple analytes, as the target labeling evolves. The real time signal is made up of two or more data points obtained over a given period of time of interest, where in certain embodiments the signal obtained is a continuous set of data points obtained continuously over a given period of time of interest.

In some embodiments, the signal is observed while the assay system is in the "wet" condition, that is, with the solution containing all the unknowns still in contact with the assay detection system. As such, there is no need to wash away all of the non-binding or irrelevant molecules. This "wet" detection is possible because the magnetic field generated by the magnetic tag nanoparticle (e.g., 100 nm or less as described elsewhere) decreases rapidly as the distance from the nanoparticle increases. Therefore, the magnetic field at the sensor of the nanoparticle bound to the captured target molecule exceeds the magnetic field from the unbound magnetic nanoparticles in the solution, which are both at a greater distance from the detector and are in Brownian motion. The term "proximity detection" as used herein refers to this dominance at the sensor of the bound nanoparticles. Under the "proximity detection" scheme specifically absorbed analyte-nanotag conjugates at the sensor surface can be quantified without washing off the nonspecific magnetic nanotags in the solution. Furthermore, in certain embodiments, with appropriate surface chemistry and capture probes, the same magneto-nano biosensors for either protein or nucleic acid assays can be employed.

The magnetic nanotag binding kinetics can be approximately described by the following equation:

$$n = \frac{n_o(e^{k_{on}C_0 t} - 1)}{e^{k_{on}C_0 t}} = n_0(1 - e^{-k_{on}C_0 t}),$$

where n (cm$^{-2}$) is the density of captured streptavidin-coated nanotags, $n_o$ is the original density of biotinylated linker antibodies on the sensor surface before the nanotag application, $k_{on}$ (cm$^3$s$^{-1}$) is the association rate constants for the specific absorption of nanotags on the sensor surface, and $C_0$ is the nanotag concentration in the bulk solution away from the sensor surface. The initial slope of the real-time signal trace at the moment of nanotag application is described by the following equation:

$$\frac{dn}{dt}\bigg|_{t=0} = k_{on}C_0 n_0.$$

Since $k_{on}C_0$ is a constant for a given nanotag solution, the initial slope is directly proportional to the biotinylated linker antibody density $n_0$, which is in turn directly proportional to the analyte density captured on the sensor surface. Therefore, in certain embodiments, instead of using voltage signal from magneto-nanosensors, the initial slope of the real-time signal trace can be used to quantify analyte concentrations. Furthermore, the slope of the real-time signal trace at any time instant t can be derived as follows:

$$\frac{dn}{dt}\bigg|_{t=0} = k_{on}C_0 n_0 e^{-k_{on}C_0 t}.$$

Therefore, the slope at an appropriate time t can be used to quantify analytes as long as the time instant t and constant $k_{on}C_0$ are kept the same for standard curves and real assays.

In certain cases, the magnetic nanoparticles in magnetic assays can precipitate, especially when the particle sizes are greater than about 100 nm or when the biofunctionalization of the nanotags is not robust. In these cases, nanotag kinetics can be described as follows:

$$n = n_0(1 - e^{-k_{on}C_0 t}) + k_{ns}C_0 t,$$

where $k_{ns}$ is a constant characterizing the nonspecific absorption of magnetic nanotags due to precipitation. In certain embodiments, readings in the presence of precipitated nanoparticles can be achieved by simultaneously recording the real-time signal traces of a probe sensor (positive sensor) and a control sensor (negative sensor). In these cases, the real-time signal traces of the matched pair of positive and negative sensors have similar linear slopes due to nanotag precipitation, which are essentially equal to a constant of $k_{ns}C_0$. Therefore, by subtracting the real-time signal trace of the positive sensor with that of the matched negative sensor, the specific binding signal trace, which is representative of the nanotag density (and thus analyte density) captured on the sensor surface, can be obtained.

The precipitation of nanoparticles is often caused by field introduced attraction between magnetic nanoparticles. In certain embodiments, the precipitation of nanoparticles can be reduced by improved surface modification of magnetic nanoparticles or by using smaller fields during assay to prevent aggregation of nanoparticles. If nanotags do precipitate, they tend to settle to the bottom of the flow channel due to gravity. Therefore, in certain embodiments, locating the sensors at the top of a flow cell or a microfluidic channel which carries the samples and nanotag solutions may help to reduce nonspecific signal due to precipitation.

In certain embodiments, an indirect labeling method in magnetic assays is used, i.e., nanotag labeling is done after the incubation of analytes with the magneto-nano chip. In other embodiments, a direct labeling method may be used in which the analytes are first labeled with magnetic nanotags and then incubated with the magneto-nano chip with immobilized capture probes. An aspect of both the indirect labeling method and the direct labeling method is that the proximity detection capability of the magneto-nano sensors remain substantially the same. In embodiments that employ the direct labeling method, the real time signal traces contain information about the binding kinetics of magnetic nanotag-analyte conjugates with capture probes.

Multiplex Protein Assay of Complex Samples

Aspects of the invention include the multiplex detection of the presence or absence of proteins, nucleic acids, and other analytes of interest in complex samples. For example, by "multiplex detection" is meant that two or more distinct proteins that are different from each other and have a different amino acid sequence are detected, such as 4 or more, 6 or more, 8 or more, etc., up to 20 or more, e.g., 50 or more, including 100 or more, distinct proteins. As such, in some cases, the magnetic sensor device may comprise two or more distinct magnetic sensors that each specifically detects a distinct analyte, such as four or more, 6 or more, 8 or more, etc., up to 20 or more, e.g., 50 or more, including 100 or more, distinct magnetic sensors. In certain embodiments, of interest is the multiplex detection of 2 to 20 distinct proteins, such as 4 to 20 distinct proteins. Thus, in these embodiments, the magnetic sensor device may comprise 2 to 20 distinct magnetic sensors that each specifically detects a distinct analyte, such as 4 to 20 distinct magnetic sensors. In other cases, the magnetic sensor device may comprise 20 or less distinct magnetic sensors that each specifically detects a distinct analyte, such as 10 or less, including 4 or less distinct magnetic sensors.

By "complex sample" is meant a sample that may or may not have the proteins of interest, but also includes many different proteins and other molecules that are not of interest. In certain embodiments, the complex sample is a blood sample, by which is blood or a fraction thereof, e.g., serum. In certain embodiments, the complex sample is a serum sample. In certain embodiments, the complex sample assayed in the methods of the invention is one that includes 10 or more, such as 20 or more, including 100 or more, e.g., $10^3$ or more, $10^4$ or more (such as 15,000; 20,000 or even 25,000 or more) distinct (i.e., different) molecular entities, that differ from each other in terms of molecular structure.

Systems

Systems of the invention are configured to practice the methods of analyte detection, and include magnetic sensor devices and nanotags. Magnetic sensor devices and nanotags employed in methods of the invention may be those employed in any number of magnetic detection systems including those systems based on: spin valve detectors (also referred to as spin valve film detectors), magnetic tunnel junction (MTJ) detectors, as well as those detectors described in U.S. patent application Ser. No. 10/829,505, the disclosure of which is herein incorporated by reference.

In certain embodiments, the subject magnetic sensor device comprises a substrate surface which displays magnetic sensors on the substrate surface. In some cases, the magnetic sensors have an analyte specific probe that may be adsorbed, physisorbed, chemisorbed, or covalently attached to the magnetic sensors. In certain embodiments, the magnetic sensor device comprises a substrate surface with an array of magnetic sensors.

Any given substrate may carry one, two, four or more arrays disposed on a front surface of the substrate. Depending upon the use, any or all of the arrays may be the same or different from one another and each may contain multiple distinct magnetic sensors. An array may contain one or more, including two or more, four or more, 8 or more, 10 or more, 50 or more, or 100 or more magnetic sensors. For example, 64 magnetic sensors can be arranged into an 8×8 array. In certain embodiments, the magnetic sensors can be arranged into an array with an area of less than 10 $cm^2$ or even less than 5 $cm^2$, e.g., less than about 1 $cm^2$, including less than about 50 $mm^2$, less than about 20 $mm^2$, such as less than about 10 $mm^2$, or even smaller. For example, magnetic sensors may have dimensions in the range of about 10 μm×10 μm to about 200 μm×200 μm, including dimensions of about 100 μm×100 μm or less, such as about 90 μm×90 μm or less, for instance 50 μm×50 μm or less.

In certain embodiments, the magnetic sensor may comprise a plurality of linear magnetoresistive segments, which are connected in series. For instance, the magnetic sensor can comprise 4 or more, such as 8 or more, including 16 or more, e.g. 32 or more, for example 64 or more, or 128 or more linear magnetoresistive segments. The magnetoresistive segments can each be about 5 μm wide or less, such as about 3 μm wide or less, including about 1.5 μm wide or less.

In certain embodiments, at least some, or all, of the magnetic sensors have different analyte specific probes on their surface, such that each analyte specific probe displaying magnetic sensor each specifically detects a distinct analyte. Areas in between the magnetic sensors may be present which do not carry any analyte specific probes. Such inter-sensor areas, when present, could be of various sizes and configurations.

In certain embodiments, the substrate carrying the one or more arrays will be shaped generally as a rectangular solid (although other shapes are possible), having a length of more than 4 mm and less than 150 mm, such as more than 4 mm and less than 80 mm, for instance less than 20 mm; a width of more than 4 mm and less than 150 mm, such as less than 80 mm, including less than 20 mm; and a thickness of more than 0.01 mm and less than 5.0 mm, such as more than 0.1 mm and less than 2 mm, including more than 0.2 mm and less than 1.5 mm, for instance more than about 0.8 mm and less than about 1.2 mm.

Nanoparticles

Nanoparticles useful in the practice of embodiments the present invention are magnetic (e.g., ferromagnetic) colloidal materials and particles. The magnetic nanoparticles can be high moment magnetic nanoparticles which are small in size so as to be superparamagnetic, or synthetic antiferromagnetic nanoparticles which contain at least two layers of antiferromagnetically-coupled high moment ferromagnets. Both types of nanoparticles appear "nonmagnetic" in the absence of a magnetic field, and do not normally agglomerate. In accordance with the present invention, magnetizable nanoparticles suitable for use comprise one or more materials selected from the group consisting of paramagnetic, superparamagnetic, ferromagnetic, and ferrimagnetic materials, as well as combinations thereof.

In certain embodiments, the magnetic nanoparticles possess the following properties: (1) their remnant magnetization is as small as possible so that they will not agglomerate in solutions (either superparamagnetic particles or antiferromagnetic particles can satisfy this requirement); (2) the tags display high magnetic moments under a modest magnetic field of about 100 Oe so they can be readily detected; (3) the size of the tags may be comparable to the target biomolecules so that they do not interfere with the binding interactions; (4) the tags are uniform and chemically stable in a biological environment; and/or (5) the tags are biocompatible, i.e., water soluble and functionalized so that they are readily attached to biomolecules of interest, e.g., a receptor that specifically binds to a target analyte.

In certain embodiments, the nanoparticles are high moment magnetic nanoparticles such as Co, Fe or CoFe nanocrystals which are superparamagnetic at room temperature. They can be fabricated by chemical routes such as, but not limited to salt reduction or compound decomposition in appropriate solutions. Examples of such magnetic nanoparticles have been published in the literature (S. Sun, and C. B. Murray, J. Appl. Phys., 85: 4325 (1999); C. B. Murray, et al., MRS Bulletin, 26: 985 (2001); S. Sun, H. Zeng, D. B. Robinson, S. Raoux, P. M. Rice, S. X. Wang, and G. Li, J. Am. Chem. Soc., 126, 273-279 (2004).). In certain embodiments, these particles can be synthesized with controlled size (e.g., about 5-12 nm), are monodisperse, and are stabilized with oleic acid. Magnetic nanoparticles and nanopowders suitable for use with the present invention include, but are not limited to Co, Co alloys, ferrites, cobalt nitride, cobalt oxide, Co—Pd, Co—Pt, iron, iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, and Ni alloys. In other embodiments, a thin layer of gold can be plated onto a magnetic core, or a poly-L-lysine coated glass surface can be attached to a magnetic core. Suitable nanoparticles are commercially available from, e.g., Nanoprobes, Inc. (Northbrook, Ill.), and Reade Advanced Materials (Providence, R.I.).

In some cases, magnetic nanoparticle tags are fabricated by physical methods (W. Hu, R. J. Wilson, A. Koh, A. Fu, A. Z. Faranesh, C. M. Earhart, S. J. Osterfeld, S.-J. Han, L. Xu, S. Guccione, R. Sinclair, and S. X. Wang, Advanced Materials, 20, 1479-1483 (2008)) instead of chemical routes, and are suitable for labeling the target biomolecules to be detected. The tags comprise at least two thin ferromagnetic layers, preferably $Fe_xCo_{i-x}$, wherein x is 0.5 to 0.7, or $Fe_xCo_{i-x}$ based alloys. $Fe_xCo_{i-x}$ has the highest saturation magnetization (about 24.5 kGauss) among the known ferromagnetic materials (R. M. Bozorth, Ferromagnetism, D. Van Nostrand Company (1951)). These ferromagnetic layers are separated by nonmagnetic spacer layers such as Ru, Cr, Au, etc., or their alloys. In certain cases, the spacer layers are appropriately engineered to make the ferromagnetic layers coupled antiferromagnetically so that the net remnant magnetization of the resulting particles are zero or near zero. In certain embodiments, the antiferromagnetic coupling can be achieved via RKKY exchange interaction (see e.g., S. S. P. Parkin, et al., Phys. Rev. Lett., 64(19): 2304 (1990)) and magnetostatic interaction (J. C. Slonczewski, et al., IEEE Trans. Magn., 24(3): 2045 (1988)). In some cases, the antiferromagnetic coupling strength is moderate so that the particles can be saturated (i.e., magnetization of all layers become parallel) by an external magnetic field of about 100 Oe. In some cases, this can be achieved by adjusting layer thicknesses and by alloying the spacer layer.

In particular embodiments, to facilitate the bio-conjugation of the nanoparticle, a gold cap (or cap of functionally analogous or equivalent material) is added at the top of the antiferromagnetic stack so that the nanoparticle can be conjugated to biomolecules via the gold-thiol linkage. Furthermore, appropriate surfactants can also be readily imparted to the nanoparticles, rendering them water-soluble. The edge of the nanoparticles can also be passivated with Au or other thin inert layers for chemical stability.

Any convenient protocol may be employed to fabricate the nanoparticles described above. For instance, in certain embodiments, a film stack can be made of nanometer-scale ferromagnetic and spacer layers deposited on ultrasmooth substrates (or a release layer). In some instances, a mask layer can be formed by imprinting, etching, self assembly, etc. Subsequently the mask layer and unwanted film stack are removed and cleaned off thoroughly. Then, the release layer is removed, lifting off nanoparticles which are the negative image of the mask layer. These particles are eventually imparted with surfactants and biomolecules. In some cases, the ultrasmooth substrate can be reused after thorough cleaning and chemical mechanical polishing (CMP).

In other embodiments, the nanoparticles are fabricated with a subtractive fabrication method. In this case, the film stack is directly deposited on the release layer followed by a mask layer. The film stack is etched through the mask layer, and eventually released from the substrate. These nanoparticles result from a positive image of the mask layer as opposed to the case in the additive fabrication method.

In certain embodiments, the size of the magnetic nanoparticles suitable for use with the present invention is comparable to the size of the target biomolecule to be worked with, such that the nanoparticles do not interfere with biological processes such as DNA hybridization. Consequently, the size of the magnetic nanoparticles is, in some embodiments, from about 5 nm to about 250 nm (mean diameter), such as from about 5 nm to about 150 nm, including from about 5 nm to about 20 nm. For example, magnetic nanoparticles having a mean diameter of 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 55 nm, 60 nm, 70 nm, 80 nm, 90 nm, 100 nm, 110 nm, 120 nm, 130 nm, 140 nm, and 150 nm, as well as nanoparticles having mean diameters in ranges between any two of these values, are suitable for use with the present invention. Further, in addition to a spherical shape, magnetic nanoparticles suitable for use with the present invention can be disks, rods, coils, or fibers.

In certain embodiments, synthetic antiferromagnetic nanoparticles may be larger than ordinary ferromagnetic particles. This is because, to prevent clumping, the nanoparticle must have no net magnetic moment (or a very small magnetic moment) in zero applied field. Antiferromagnetic particles may have zero magnetic moment in zero field at all sizes. In contrast, for a ferromagnetic particle, its size may be below the "superparamagnetic limit", which is, in some cases, about 20 nm or less, such as about 15 nm or less, including about 10 nm or less.

In certain embodiments, the synthetic nanoparticles described above can be produced in large quantities using a large wafer and standard vacuum thin film deposition processes. For example, with a 6-inch round wafer, 30-nm diameter nanoparticles at a rate of roughly $5 \times 10^{12}$ particles per run can be produced, assuming each particle occupies a square of 60 nm by 60 nm on the wafer.

High Sensitivity Spin Valve Detectors

A spin valve detector is a metallic multilayer thin-film structure of two ferromagnetic layers spaced by a nonmagnetic layer such as copper. One ferromagnetic layer, called the pinned layer, has its magnetization pinned to a certain direction, while the magnetization of the other ferromagnetic layer, called the free layer, can rotate freely under an applied magnetic field. The electrical resistance of a spin valve depends on the relative orientation of magnetization of the free layer to that of the pinned layer. When the two magnetizations are parallel, the resistance is the lowest; when antiparallel, the resistance is the highest. The relative change of resistance is called the magnetoresistance (MR) ratio. In some cases, the MR ratio of a spin valve can reach more than about 10% in a small magnetic field, e.g., about 100 Oe. Therefore, a spin valve can function as a sense element for the detection of a small magnetic particle that is attached to a DNA fragment as a label and immobilized onto the sensor surface. Since the particle is magnetic (under a DC bias field or AC tickling field), it generates a magnetic field. The magnetic field may then affect the orientation of the free layer magnetization, causing a change in the electrical resistance of the spin valve.

In some embodiments, the operation of a spin valve detector is described as follows: 1) The magnetic nanoparticle under a DC bias field (Hb) generates a magnetic field around it. 2) The magnetic field will affect the resistance of a spin valve closely underneath it. 3) Application of an AC tickling field (Ht) will force the moment of particle to oscillate, resulting in an oscillating MR signal from the spin valve. In some embodiments, in the in-plane mode, the spin valve detector signal due to the magnetic nanoparticle has the same frequency f as the AC tickling field Ht, while in the vertical mode the signal has twice the frequency of Ht. 4) A lock-in amplifier or frequency spectrum analyzer is used to pick up the oscillating signal with a high signal-to-noise ratio.

In certain embodiments, spin valves have a magnetoresistive (MR) ratio of about 1% to about 20%, such as about 3% to about 15%, including about 5% to about 12%. Therefore, in certain embodiments, spin vales can detect a single magnetic nanoparticle of about 10 nm size in a narrow bandwidth (i.e., about 1 Hz or less) or with lock-in detection. In these cases, by narrowing the noise bandwidth, a sufficient signal to noise ratio (SNR) is achieved even for single nanoparticle detection.

Spin valve detection may be performed with the in-plane mode (see e.g., Li, et al., J. Appl. Phys. Vol. 93 (10): 7557 (2003)). In other embodiments, the vertical mode, even though giving a slightly smaller signal amplitude, can be used when the electromagnetic interference (EMI) signal due to the AC tickling field in the detection system is significant. The EMI signal tends to center at the frequency f of the AC tickling field, so it can be eliminated or greatly reduced if by performing lock-in detection at the frequency 2f. Furthermore, in some instances, a 2-bridge circuit can be used to eliminate any remaining EMI. Even more sophisticated signal acquisition and processing methods with an AC modulation sense current and an AC tickling field at two different frequencies have been published (e.g., S-J Han, H. Yu, B. Murmann, N. Pourmand, and S. X. Wang, IEEE International Solid-State Circuits Conference (ISSCC) Dig. Tech. Papers, San Francisco Marriott, Calif., USA, Feb. 11-15, 2007.)

In certain embodiments, the signal from the spin valve detector due to the magnetic tag depends on the distance between the magnetic tags and the free layer of the spin valve, in addition to the geometry and bias field of the spin valve itself. The detector voltage signal from a single magnetic particle decreases with increasing distance from the center of the particle to the midplane of the spin valve free layer.

In certain embodiments, the free layer in the spin valves is on top of the pinned layer to facilitate detection of the magnetic nanoparticles because the sensing magnetic field from a magnetic particle drops monotonically with the distance between the sensor and the particle. Furthermore, minimization of the distance between the magnetic particle and the top surface of the free layer, including the thickness of the passivation layer protecting the spin valves facilitates magnetic particle detection.

In some instances, during operation of the detector array, a solution of DNA (or protein) is flowed over the sensor surface to allow for affinity binding of analytes of interest with corresponding capture agents on the sensor. Therefore, corrosion of the sensor surface is a concern because degradation of the detector surface could reduce sensitivity by reducing the signal from biological binding events or by degrading the detectors themselves.

In certain embodiments, to reduce the corrosion of the sensor surface, magnetic detection schemes may include the addition of relatively thick passivation layers to the detector surfaces. A trade-off occurs between retaining high sensitivity while sufficiently guarding against degradation. Thus, in certain embodiments, the detector combines an ultrathin (i.e., about 10 nm or less) layer of passivation and very small magnetic nanoparticle tags (i.e., with a mean diameter of about 20 nm or smaller), thus achieving a particle-center-to-detector distance of less than about 30 nm (including the intervening DNA fragment length of about 10 nm), which is close enough to provide the necessary sensitivity for single-tag detection. In certain embodiments, the ultrathin layers of passivation (such as Ta, Au, or oxide) suitable for use with the presently disclosed detectors can have a thickness from about 1 nm to about 10 nm, such as from about 1 nm to about 5 nm, including from about 1 nm to about 3 nm. In certain embodiments, the ultrathin layers of passivation (such as Ta, Au, or oxide) suitable for use with the presently disclosed detectors can have a thickness from about 10 nm to about 50 nm, such as from about 20 nm to about 40 nm, including from about 25 nm to about 35 nm.

High Sensitivity Magnetic Tunnel Junction (MTJ) Detectors

An MTJ detector is constructed similarly to a spin valve detector except that the non-magnetic spacer is replaced with a thin insulating tunnel barrier such as alumina or MgO and that the sense current flows perpendicular to the film plane. Electron tunneling between two ferromagnetic electrodes is controlled by the relative magnetization of the two ferromagnetic electrodes, i.e., tunneling current is high when they are parallel and low when antiparallel. In certain embodiments, the MTJ detector is composed of a bottom electrode, magnetic multilayers including a tunnel barrier, and a top electrode. In some cases, MTJ detectors have magnetoresistance ratios exceeding 200% (S. Ikeda, J. Hayakawa, Y. M. Lee, F. Matsukura, Y. Ohno, T. Hanyu, and H. Ohno, IEEE TRANSACTIONS ON ELECTRON DEVICES, VOL. 54, NO. 5, 991-1001 (2007)) and inherently large device resistances, yielding higher output voltage signals.

In certain embodiments, the MJT detector has a double-layer top electrode. The first layer can be a thin gold layer (about 10 nm or less), which facilitates binding DNA or protein capture probes. The second layer can be aluminum, copper or other conductive metals which do not bind with biomolecular probes, including but not limited to palladium, palladium alloys, palladium oxides, platinum, platinum alloys, platinum oxides, ruthenium, ruthenium alloys, ruthenium oxides, silver, silver alloys, silver oxides, tin, tin alloys, tin oxides, titanium, titanium alloys, titanium oxides, and combinations thereof. In some instances, an aperture in the second layer, slightly smaller in size than the MTJ, is created either by a lift-off process or by etching a uniform second layer. In these embodiments, the distance between the nanoparticle tag and the top surface of the free magnetic layer can range from about 6 nm to about 100 nm, such as about 6 nm to about 40 nm, including from about 6 nm to about 30 nm, such as from about 6 nm to about 20 nm, including from about 6 nm to about 10 nm. Furthermore, this arrangement may facilitate the reduction or prevention of current crowding (see e.g., van de Veerdonk, R. J. M., et al., Appl. Phys. Lett., 71: 2839 (1997)) within the top electrode which may occur if only a very thin gold electrode is used.

Except that the sense current flows perpendicular to the film plane, the MTJ detector can operate similarly to the spin valve detector, either with in-plane mode or vertical mode. As discussed above regarding spin valve detectors, in certain embodiments, the vertical mode can be used for EMI rejection and, similarly, ultrathin passivation also applies to MTJ detectors. In addition, the first top electrode of thin gold on MTJ detectors can also serve the triple purposes of electrical conduction, ultrathin passivation, as well as specific biomolecular probe attachment.

In certain embodiments, at the same detector width and particle-detector distance, MTJ detectors can give larger signals than spin valve detectors. For example, for an MTJ detector with a junction area of 0.2 µm by 0.2 µm and resistance-area product of 1 kOhm-µm$^2$, operating with a MR of 250% at a bias voltage of 250 mV, and Hb=35 Oe, Ht=100 Oe rms, the voltage signal from a single 11 nm diameter Co nanoparticle whose center is 35 nm away from the free layer midplane is about 200 µV, which in some instances is more than an order of magnitude larger than those for similar-sized spin valve detectors.

Utility

The subject methods, systems and kits find use in a variety of different applications where determination of the presence or absence, and/or quantification of one or more analytes in a sample is desired. In certain embodiments, the methods are directed to detection of a set of biomarkers, e.g., 2 or more distinct protein biomarkers, in a sample. For example, the methods of invention may be used in the rapid, clinical detection of 2 or more disease biomarkers in a serum sample, e.g., as may be employed in the diagnosis of a disease condition in a subject, in the ongoing management or treatment of a disease condition in a subject, etc.

In certain embodiments, the subject methods, systems and kits find use in detecting biomarkers. In some cases, the subject methods, systems and kits may be used to detect the presence or absence of particular biomarkers, as well as an increase or decrease in the concentration of particular biomarkers in blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject methods and systems. Furthermore, the early detection of biomarkers associated with diseases is facilitated by the picomolar and/or femtomolar sensitivity of the subject methods and systems. Due to the capability of detecting multiple biomarkers on a single chip, combined with sensitivity, scalability, and ease of use, the presently disclosed assay methods and systems finds use in portable and point-of-care or near-patient multiplexed molecular diagnostics.

In certain embodiments, the subject methods, systems and kits find use in detecting biomarkers for a disease or disease state. In some cases, the disease is a cellular proliferative disease, such as but not limited to, a cancer, a tumor, a papilloma, a sarcoma, or a carcinoma, and the like. Thus, the subject methods, systems and kits find use in detecting the presence of a disease, such as a cellular proliferative disease, such as a cancer, tumor, papilloma, sarcoma, carcinoma, or the like. In certain instances, particular biomarkers of interest for detecting cancer or indicators of a cellular proliferative disease include, but are not limited to the following: C-reactive protein, which is an indicator of inflammation; transcription factors, such as p53, which facilitates cell cycle and apoptosis control; polyamine concentration, which is an indicator of actinic keratosis and squamous cell carcinoma; proliferating cell nuclear antigen (PCNA), which is a cell cycle related protein expressed in the nucleus of cells that are in the proliferative growth phase; growth factors, such as IGF-I; growth factor binding proteins, such as IGFBP-3; micro-RNAs, which are single-stranded RNA molecules of about 21-23 nucleotides in length that regulate gene expression; carbohydrate antigen CA19.9, which is a pancreatic and colon cancer biomarker; prostate specific membrane antigen, which is a prostate cancer biomarker; cyclin-dependent kinases; epithelial growth factor (EGF); vascular endothelial growth factor (VEGF); protein tyrosine kinases; overexpression of estrogen receptor (ER) and progesterone receptor (PR); and the like.

In certain embodiments, the subject methods, systems and kits find use in detecting biomarkers for an infectious disease or disease state. In some cases, the biomarkers can be molecular biomarkers, such as but not limited to proteins, nucleic acids, carbohydrates, small molecules, and the like. Particular diseases or disease states that may be detected by the subject methods, systems and kits include, but are not limited to, bacterial infections, viral infections, increased or decreased gene expression, chromosomal abnormalities (e.g. deletions or insertions), and the like. For example, the subject methods, systems and kits can be used to detect gastrointestinal infections, such as but not limited to, aseptic meningitis, botulism, cholera, *E. coli* infection, hand-foot-mouth disease, helicobacter infection, hemorrhagic conjunctivitis, herpangina, myocaditis, paratyphoid fever, polio, shigellosis, typhoid fever, vibrio septicemia, viral diarrhea, etc. In addition, the subject methods, systems and kits can be used to detect respiratory infections, such as but not limited to, adenovirus infection, atypical pneumonia, avian influenza, bubonic plague, diphtheria, influenza, measles, meningococcal meningitis, mumps, parainfluenza, pertussis (i.e., whooping chough), pneumonia, pneumonic plague, respiratory syncytial virus infection, rubella, scarlet fever, septicemic plague, severe acute respiratory syndrome (SARS), tuberculosis, etc. In addition, the subject methods, systems and kits can be used to detect neurological diseases, such as but not limited to, Creutzfeldt-Jakob disease, bovine spongiform encephalopathy (i.e., mad cow disease), Parkinson's disease, Alzheimer's disease, rabies, etc. In addition, the subject methods, systems and kits can be used to detect urogenital diseases, such as but not limited to, AIDS, chancroid, *Chlamydia*, condyloma accuminata, genital herpes, gonorrhea, lymphogranuloma venereum, non-gonococcal urethritis, syphilis, etc. In addition, the subject methods, systems and kits can be used to detect viral hepatitis diseases, such as but not limited to, hepatitis A, hepatitis B, hepatitis C, hepatitis D, hepatitis E, etc. In addition, the subject methods, systems and kits can be used to detect hemorrhagic fever diseases, such as but not limited to, Ebola hemorrhagic fever, hemorrhagic fever with renal syndrome (HFRS), Lassa hemorrhagic fever, Marburg hemorrhagic fever, etc. In addition, the subject methods, systems and kits can be used to detect zoonosis diseases, such as but not limited to, anthrax, avian influenza, brucellosis, Creutzfeldt-Jakob disease, bovine spongiform encephalopathy (i.e., mad cow disease), enterovirulent *E. coli* infection, Japanese encephalitis, leptospirosis, Q fever, rabies, sever acute respiratory syndrome (SARS), etc. In addition, the subject methods, systems and kits can be used to detect arbovirus infections, such as but not limited to, Dengue hemorrhagic fever, Japanese encephalitis, tick-borne encephalitis, West Nile fever, Yellow fever, etc. In addition, the subject methods, systems and kits can be used to detect antibiotics-resistance infections, such as but not limited to, *Acinetobacter baumannii, Candida albicans, Enterococci* sp., *Klebsiella pneumoniae, Pseudomonas aeruginosa, Staphylococcus aureus*, etc. In addition, the subject methods, systems and kits can be used to detect vector-borne infections, such as but not limited to, cat scratch disease, endemic typhus, epidemic typhus, human ehrlichosis, Japanese spotted fever, louse-borne relapsing fever, Lyme disease, malaria, trench fever, Tsutsugamushi disease, etc.

Similarly, the subject methods, systems and kits can be used to detect cardiovascular diseases, central nervous diseases, kidney failures, diabetes, autoimmune diseases, and many other diseases.

Kits

Also provided are kits for practicing one or more embodiments of the above-described methods. The subject kits may vary greatly, and may include various devices and reagents. Reagents and devices of interest include those mentioned herein with respect to magnetic sensor devices, magnetic nanoparticles, binding agents, buffers, etc.

In certain embodiments, the subject kits include a magnetic sensor device and a magnetic label. In these embodiments, the magnetic sensor device comprises an analyte specific probe displaying magnetic sensor which displays a probe that specifically binds to an analyte on a surface thereof, and a processor configured to obtain a real-time signal from the magnetic sensor to determine whether the analyte is present in a sample. In some embodiments, the magnetic sensor comprises an ultrathin passivation layer, where in certain cases the passivation layer has a thickness of about 40 µm or less, such as about 30 µm or less, including about 20 µm or less. In further embodiments of the subject kits, the sensor is a spin valve sensor, and in other embodiments of the subject kits, the sensor is a magnetic tunnel junction sensor. In certain cases, the magnetic label of the subject kits is a magnetic nonotag.

In certain embodiments, the subject kits include a magnetic sensor device that comprises two or more distinct magnetic sensors that each specifically detects a distinct analyte, such as four or more, 6 or more, 8 or more, etc., up to 20 or more, e.g., 50 or more, including 100 or more, distinct magnetic sensors. Thus, the subject kits find use in the multiplex detection of the presence or absence, and/or quantification of proteins, nucleic acids, or other analytes of interest in complex samples.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the Internet to access the information at a removed site. Any convenient means may be present in the kits.

The following examples are offered by way of illustration and not by way of limitation.

EXPERIMENTAL

I. Methods

A. Chip Fabrication—On silicon wafers with 150 µm thermal oxide, a spin valve film with a layer sequence similar to that of hard disk drives read heads was patterned by ion milling into individual sensors (S. X. Wang and G. Li, IEEE Trans. Magn., vol. 44, no. 7, 1687-1702 (2008)), each consisting of 32 linear segments of 1.5×100 µm connected in series and arranged to cover an area of 100×100 µm$^2$ (see FIG. 4). Each sensor had a nominal resistance of 40 kf2 and a maximum magnetoresistance of 12%. Corrosion resistant leads (Ta 5/Au 300/Ta 5) nm were sputter deposited and patterned by lift-off. As suggested elsewhere (Schmitt, G. et al. Passivation and corrosion of microelectrode arrays. Electrochim Acta 44, 3865-3883 (1999)), the sensors were passivated with a tri-layer oxide ($SiO_2$ 10/$Si_3N_4$10/$SiO_2$ 10 nm), which was deposited at room temperature by ion beam sputter deposition. The leads were passivated with an additional tri-layer oxide ($SiO_2$ 100/$Si_3N_4$ 100/$SiO_2$ 100 nm). A two-component epoxy (EP5340, Eager Plastics, Chicago, Ill.) was used to assemble the chip and reagent well (Tygon® tubing, ¼" ID×⅜" OD, 6 mm long) on the ceramic 84-pin chip carrier (LCC08423, Spectrum Semiconductor Materials, San Jose, Calif.). A layer of about 0.5 mm of the same epoxy was used to mask some of the sensors (see FIG. 4), so as to create two adjacent but separate sites for subsequent biofunctionalization. The masked sensors, no longer able to detect nanotag binding, serve as electrical signal references (see section G, below).

B. Surface Preparation—The assembled chips were thoroughly washed with acetone, methanol, isopropanol, and de-ionized water. A ten minute UV ozone treatment (UVO Cleaner Model 42, Jelight, Irvine, Calif.) was used to remove organic residues. To form the base layer of the biofunctionalization, a 2% solution of polyethyleneimine (PEI, CAS 9002-98-6, Sigma-Aldrich) in deionized water was applied to the chip surface for 2 minutes. The chips were then rinsed with deionized water and then baked at 150° C. for 5 minutes to solidify the adsorbed PEI.

C. Muliplex Protein Assays—Up to four different probes were manually deposited in the form of 1 µL droplets, containing antibodies (Anti-IL-10, Anti-IL-1α, Anti-TNF-α, and Anti-VEGF) at a concentration of 500 µg/mL, onto different areas of the chip to functionalize the sensor array. Additional control sensors were functionalized with a 1 µL droplet of BSA 100 mg/mL. The sensor functionalizations were incubated for 30 minutes at 4° C. and 95% relative humidity. The chips were then rinsed twice with blocking buffer (1% BSA, 0.2% Tween 20, in PBS) to block any remaining non-specific surface binding sites. Samples were prepared by diluting the protein analytes (TNF-α, 17.5 kDa; IL-10, 18.5 kDa; IL-1α, 18 kDa) in either PBS buffer or in 50% human serum (balance PBS) to the desired concentrations. 100 µL of sample solution were pipetted into the reagent well of a chip and incubated for 1 hour at room temperature. Subsequently, the chip was rinsed twice with blocking buffer (0.1% BSA, 0.2% Tween 20, in PBS). A multiplex linker antibody solution was prepared consisting of four biotinylated antibodies, one for each potential analyte, at a concentration of 2 µg/mL in PBS. 100 µL of this linker antibody solution were incubated in the reagent well of the chip for 1 hour at room temperature. With the linker solution still in place, the chips were then transferred over to the measuring station for MNT-based analyte quantification.

D. hCG Assays—All chips were uniformly functionalized with a single capture probe, anti-human-hCG 1 mg/mL, incubated overnight at 4° C., then rinsed twice with blocking buffer. Pure serum samples spiked with hCG to 2.5, 25, 250, and 2,500 IU/L were supplied by the U.S. National Cancer Institute and diluted 1:1 with PBS buffer. Analyte incubation time was 1 hour, and linker antibody, 5 µg/mL in PBS, was incubated for 90 minutes. With the linker solution still in place, the chips were then transferred over to the measuring station for MNT-based analyte quantification. The concentrations of hCG after dilution with PBS have been converted using 1 IU/L=1.9 pM (Birken, S. et al. Preparation and characterization of new WHO Reference Reagents for human chorionic gonadotropin and metabolites. Clin. Chem. 49, 144-154 (2003); Sturgeon, C. M. & Ellis, A. R. Standardization of FSH, LH and hCG—Current position and future prospects. Mol. Cell. Endocrinol. 260, 301-309 (2007)).

E. MNT-Based Analyte Quantification—To remove the linker antibody solution and to confirm signal baseline stability, the chips were rinsed with MNT-free PBS buffer several times. While the associated wet/dry transitions did occasionally shift the baseline slightly, these shifts were reversible and usually negligible compared to the signals of interest. The absolute signal level on contact with MNT-free buffer was taken to be zero. The MNT-free buffer solution was then aspirated from the well and replaced with 50 µL of streptavidin-coated MNT stock solution (MACS 130-048-102, Miltenyi Biotec). The nanotag solution was incubated without stirring for the next 20 minutes at room temperature. The signal levels at the end of this 20 minute nanotag incubation time were taken as the final result of the assay.

F. Optional Nanotag Amplification—At the end of the initial 20 minute MNT incubation period, the well was rinsed five times with PBS, and then re-filled with 50 µL of the biotinylated linker antibody solution. This solution was incubated for five minutes, attaching biotinylated antibodies to the already adsorbed MNTs. Since these linker antibodies can have multiple biotin sites, new binding sites for additional MNTs were created this way on the existing MNTs. After five minutes, the solution was aspirated, the well rinsed five times with PBS, and 50 µL of MNT stock solution were added, resulting in the generation of an additional MNT binding signal. This amplified the signal levels by a factor of about 2× with each iteration.

G. Electronics—An alternating current of 7 $\mu A_{rms}$ at 500 Hz was applied to each sensor. An alternating in-plane tickling field of 80 $Oe_{rms}$ at 208 Hz was applied perpendicular to the sensor segments to establish a magnetic signal baseline, which is minimally perturbed in the vicinity of any nanotags. This perturbation of baseline signal is our net signal. A steady bias field of 50 Oe was also applied along the longitudinal direction of the sensor segments to facilitate a coherent (low noise) rotation of the sensor's magnetic domains in response to the 208 Hz tickling field. The signal level was measured by performing a fast Fourier transform of the voltage across each sensor once every 2 seconds and recording the magnitude of the (amplitude modulation generated) 708 Hz spectral component, which in this setup is primarily a measure of the alternating magnetic tickling field strength in the immediate vicinity of the sensor. To reduce the common mode and sensor drift, every functionalized sensor was measured differentially against a reference sensor, i.e., against a sensor which was covered with a layer of epoxy thick enough to positively prevent any MNT detection. Additional details of this measurement setup are described elsewhere (Han, S. J., Xu, L., Wilson, R. J. & Wang, S. X. A novel zero-drift detection method for highly sensitive GMR biochips. IEEE Trans. Magn. 42, 3560-3562 (2006)).

II. Results & Discussion

In certain embodiments, magnetic nanotag (MNT)-based biomolecular assays are capable of fast and sensitive multiplex protein detection involving serum samples.

Micron-sized labels may diffuse slowly, are prone to magnetic interaction and subsequent precipitation, and are bulky compared to nanometer-sized analyte molecules. In contrast, in certain embodiments, nanometer sized MNTs may be used, such as commercially available 50 nm MACS MNTs, which have a very small magnetic signature but which exhibit long term suspension stability and excellent binding selectivity. In some cases, to enhance the sensitivity of the assay, the passivation of the SV sensors can be thinned to about 30 nm or less. The resulting sensitivity allows the reliable detection of minute magnetic signatures, such as from MACS MNTs, provided that they are in the immediate proximity of the sensor. By combining small magnetic moment MNTs with very sensitive proximity detection, the sensors disclosed herein primarily detect MNTs that are bound to the sensor surface. If unbound MNTs are stable in suspension, then the signal contribution from these extraneous unbound MNTs is negligible, and washing steps, which are typically required to remove unbound signal-generating labels, can be omitted. In practice, this suppression of unbound labels means that the true amount of currently bound nanotags can be observed in real-time, and that negative control sensors experience no signal shift during nanotag application and removal. Thus, in certain embodiments, simple one-step homogeneous assays with no washing steps are provided, which find utility in clinical applications.

Methods for early cancer detection via quantification of cancer-related cytokines are also provided. Analytes to be detected in the MNT-based protein assay include, but are not limited to vascular endothelial growth factor (VEGF), tumor necrosis factor alpha (TNF-α), interleukin-10 (IL-10), and interleukin-1-alpha (IL-1α).

FIG. 1 shows a schematic of the detection scheme in which analyte is captured on the sensor surface and quantified with streptavidin-coated MNTs. Probe sensors were functionalized with capture antibodies specific to the chosen analyte, while control sensors were blocked with a 10 wt % BSA solution (FIG. 1a). During analyte incubation, the probe sensors captured a fraction of the analyte molecules (FIG. 1b). A biotinylated linker antibody was subsequently incubated which binds to the captured analyte (FIG. 1c), and which provides binding sites for the streptavidin-coated magnetic nanotags. Streptavidin-coated magnetic nanotags were then incubated (FIG. 1d), and the nanotag binding signal, which saturates at an analyte concentration-dependent level, was used to quantify the analyte concentration.

In some cases, the analyte and linker antibody incubation time (FIGS. 1b, 1c) is one hour or less, while the MNT-based quantification (FIG. 1d) requires less than fifteen minutes. In certain embodiments, the total assay time can be reduced to below 30 minutes, for example through analyte incubation in a microfluidic channel, so that the methods may suitable for a physician office laboratory or point-of-care applications. In some cases, the MNT detection scheme can be carried out on a chip, which has an array of 64 SV sensors and a 200 µL reaction well placed on top (see FIG. 4), so that the reagents can be pipetted and aspirated easily. In certain cases, the electronic instrumentation is able to record and display 16 sensor signals per chip in real-time, with an update rate of 0.5 Hz per sensor. In some cases, two of the 16 measured sensors are covered with epoxy and used to record an electronic reference signal, so that 14 sensors per chip can be used to record assay signals.

Figure 2:
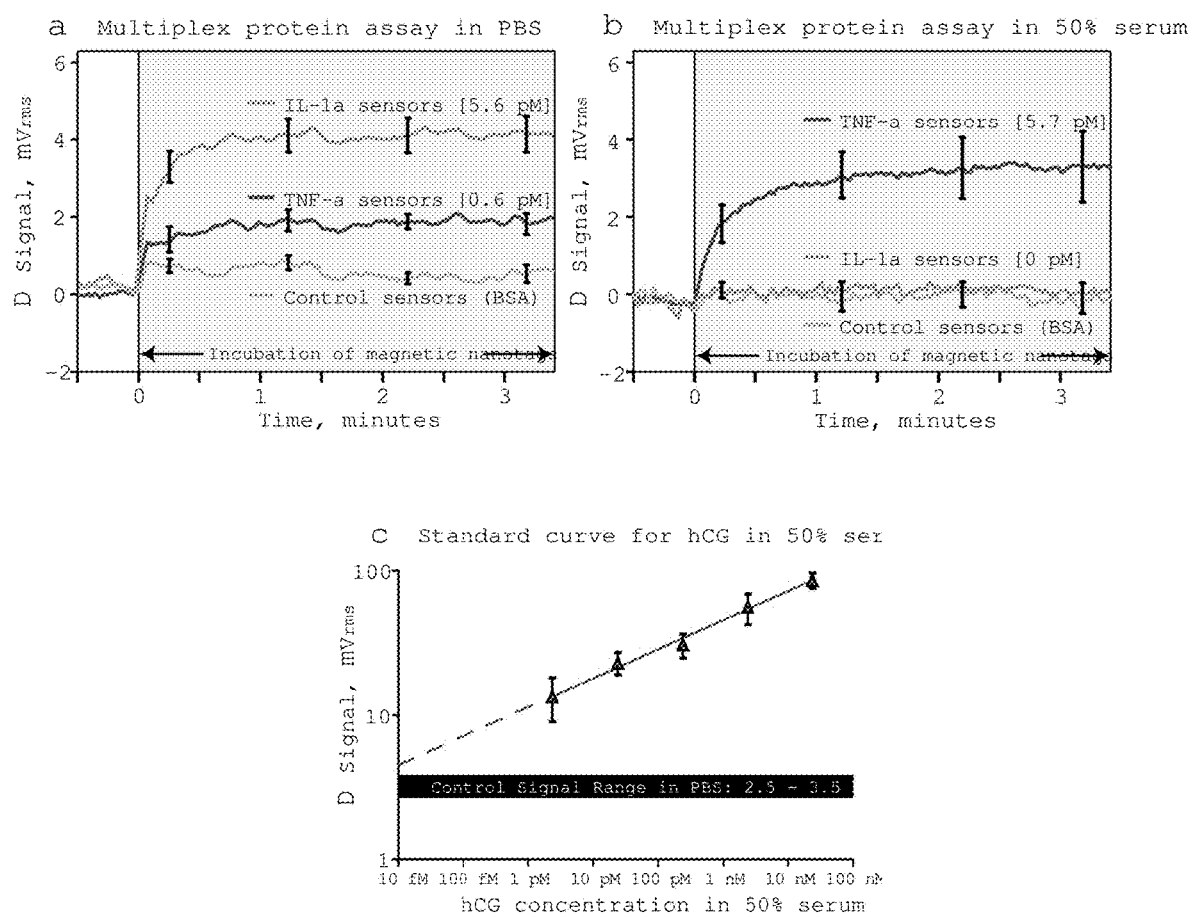
FIG. 2 shows graphs from the results of multiplex MNT-based assays.

Actual binding curve (signal vs. time) data from MNT-based immunoassays with multiple probes is shown in FIG. 2. The average signal±1 S.D. (standard deviation) is shown. The time t=0 defines the moment of MNT nanotag application in the final step of the assay. Beginning at t=0, the signal rise reflects the binding of MNTs to the SV sensor surface in real-time. As a result of the indirect labeling method used here, the real-time data contains information about the MNT binding kinetics rather than the analyte binding kinetics, but the saturation level of an MNT binding curve is taken as a direct measure of binding site abundance on the sensor surface, which in turn is determined by the concentration of the previously applied analyte. In addition to analyte quantification, the real-time MNT binding curves are also used to identify and eliminate sources of error, as they help to distinguish proper (i.e., continuous, steady, saturating) from improper (i.e., discontinuous, noisy, drifting) sensor operation. For example, in some cases, the signal quickly stabilizes despite an excess amount of nanotags in the solution, which indicates that in the absence of suitable binding sites, the nanotags do not precipitate or bind spontaneously. This facilitates precise analyte quantification. The MNT binding curves also give the time needed for reaching signal saturation, i.e., MNT binding equilibrium. In certain embodiments, the net signal gains at time t=15 minutes are reported to compare different assay runs, but when few MNT binding sites are available (i.e., due to low analyte concentration), MNT quantification can reach equilibrium in as little as 60 seconds.

An example of such rapid MNT quantification can be seen in FIG. 2a. In this experiment (FIG. 2a), fourteen sensors on a chip were functionalized as follows: 4 sensors anti-IL-1α, 8 sensors anti-TNF-α, and 2 sensors BSA. A sample consisting of 5.6 pM IL1-α and 0.6 pM TNF-α in PBS was then incubated for one hour. The resulting binding signals level off approximately one minute after MNT application, and the signal levels of 1.9 µV for TNF-α (8 sensors) and 4.1 µV for IL-1α (4 sensors) are significantly larger and distinct from the non-specific signal of 0.6 µV on the BSA-functionalized control sensors.

In another experiment (FIG. 2b), a chip was similarly functionalized: 5 sensors anti-TNF-α, 2 sensors anti-IL-1α, and 2 sensors BSA. However, in this experiment the sample consisted of 5.7 pM TNF-α in 50% serum, balance PBS. Both the sensors blocked with BSA and the IL-1α sensors were negative controls. The resulting average signal saturated at 3.2 µV after about two minutes. The negative controls, consisting of both the anti-IL-1α and BSA functionalized sensors, showed an average of 0.1 µV (range +0.3 µV to −0.3 µV), which indicates an average signal to background ratio of 32:1 at this concentration.

To demonstrate the signal vs. concentration scaling relationship of an analyte in 50% serum over large changes in analyte concentration, a series of MNT-based immunoassays were performed to detect human chorionic gonadotropin (hCG) which was spiked into 50% serum. In this experiment, five chips were functionalized with anti-hCG and then exposed to different concentrations of hCG in 50% serum. Fourteen sensors were measured per chip (see FIG. 2c). In this case, hCG was chosen as a model analyte because reference hCG samples, high quality antibodies, and comparable commercial hCG assays are readily available. The results are shown in FIG. 2c. The lowest hCG concentration, 2.4 pM in 50% serum, resulted in a 14-sensor median signal of 13.6 µV (max=27 µV, min=8.2 µV, SD=4.6 µV). In addition, for each ten-fold increase in hCG concentration, the signal approximately doubled. The results demonstrate the detection of hCG concentrations over at least four orders of magnitude, down to the serum baseline level, which is about 1 pM.

Performing the same assay and label amplification in analyte-free PBS (see FIG. 2b control assay) shows that the control signal is in a range of about 2.5 $\mu V_{rms}$ to about 3.5 $\mu V_{rms}$ which is significantly lower than the signal expected from 1 pM hCG in serum. Extrapolation of the scaling trend down to the background level indicates that the MNT-based assay can detect about 10 femtomolar concentrations of hCG in serum, which is more sensitive than commercial ELISA kits (i.e., with a sensitivity of about 4 pM). In certain embodiments, higher signal levels can be achieved by successively adsorbing two or more layers of nanotags (e.g. three layers of nanotags) by in situ nanotag amplification. The nanotag amplification uniformly elevates all signal levels, including the control signal, thus nanotag amplification facilitates the detection of signals which are initially too low to be precisely quantified. In some cases, the relative signal vs. concentration scaling relationship remained unchanged by nanotag amplification.

Figure 3:
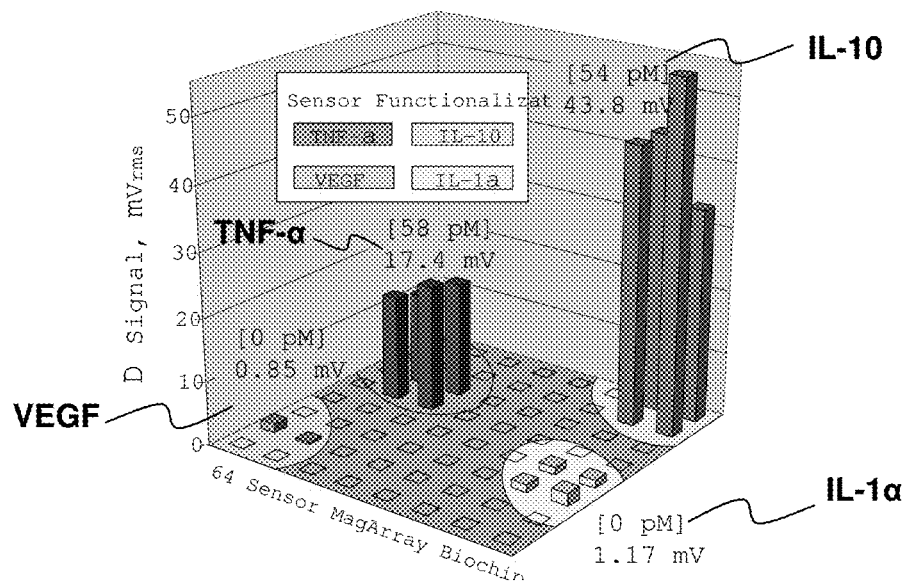
FIG. 3 shows the results of a quadplex protein assay.

FIG. 3 shows the results of a multi-analyte, multi-probe assay performed on a single chip. In this experiment, four regions of the chip were functionalized, each with one of four capture antibodies (anti-TNF-α, anti-IL-10, anti-VEGF, and anti-IL-1α). The chip was then exposed to a subset of the four potentially recognized analytes, namely TNF-α 58 pM and IL-10 at a concentration of 54 pM in PBS. Thus, the VEGF sensors and the IL-1α sensors served as negative controls. Fourteen sensors were subsequently chosen from the sensor array to measure the signals from each of the four regions with a certain redundancy (ranging from replicate to quadruple). The initial MNT quantification was enhanced with one round of nanotag amplification. As seen in FIG. 3, only the sensors with matching analytes (in this case, TNF-α and IL-10) gave large signals as expected. Signal variation among sensors with identical functionalization was small. In certain embodiments, the chip's sensitivity appears to vary with the type of functionalization, since IL-10 was observed to give a larger signal than TNF-α at similar concentrations. This indicates that, in certain cases, the analyte affinity of each functionalization can be different. In some cases, the small but non-zero signals on the VEGF and IL-1α sensors may be due to a small amount of cross-reactivity, which depends on the matching and quality of the assay antibodies.

In certain embodiments, with carefully screened antibodies, the MNT-based analyte quantification method can be used for clinically relevant protein detection in real world serum samples, and multiplex protein detection can be readily performed with this method. In some cases, up to 256 different probes, including up to 128, for instance up to 64 different probes can be accommodated and simultaneously measured. In some cases, as discussed above, the sensor can be a spin valve sensor or a magnetic tunnel junction sensor.

In addition, as discussed in more detail below, sensitivity can be increased by using sensors with narrower segments (see FIG. 7). Furthermore, the analytic sensitivity of MNT-based assays capture agents can be enhanced further with higher affinity, and similarly small but higher magnetic moment MNTs. Due to the capability of detecting multiple biomarkers on a single chip, combined with sensitivity, scalability, and ease of use, the presently disclosed protein assay method finds use in portable and point-of-care or near patient multiplexed molecular diagnostics. In addition, in certain embodiments, SV sensors are pH-insensitive, with no "bleaching" of MNTs and no magnetic background from bio-systems. In some cases, MNT-based assays produce signals that are stable even during changes of experimental conditions, such as wet to dry transitions. In other embodiments, MNT-based analyte quantification can also be combined with magnetic separation techniques. For example, analyte extraction and the first round of molecular amplification can be combined into a single magnetic separation step to achieve an ultra-sensitive protein detection. Magnetic forces can also be used to draw MNT-labeled analytes towards the sensors, thereby reducing diffusion distances and assay time and improving sensitivity.

Figure 4:
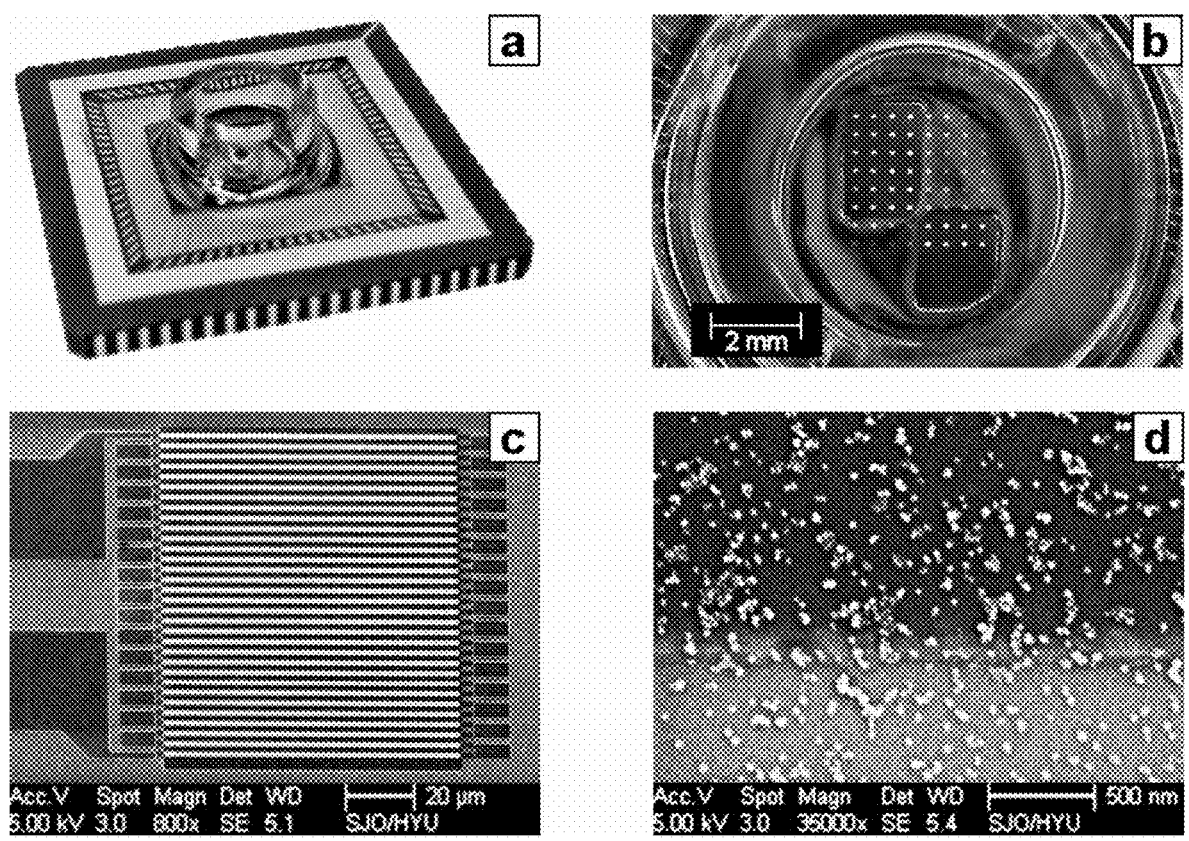
FIG. 4 shows a magnetic nanotag-based protein assay chip.

FIG. 4 shows a magnetic nanotag-based protein assay chip. The chip has a 200 µL reaction well and is supported by an 84-pin ceramic base (see FIG. 4a). Embedded in the bottom of the reaction well are 64 sensors in an 8×8 array (see FIG. 4b). Each sensor has an active area of roughly 90×90 $\mu m^t$ and consists of 32 linear magnetoresistive segments, each 1.5 µm wide, which are connected in series (see FIG. 4c). FIG. 4d shows the edge of one such sensor segment and bound nanotags imaged with a scanning electron microscope.

Figure 5:
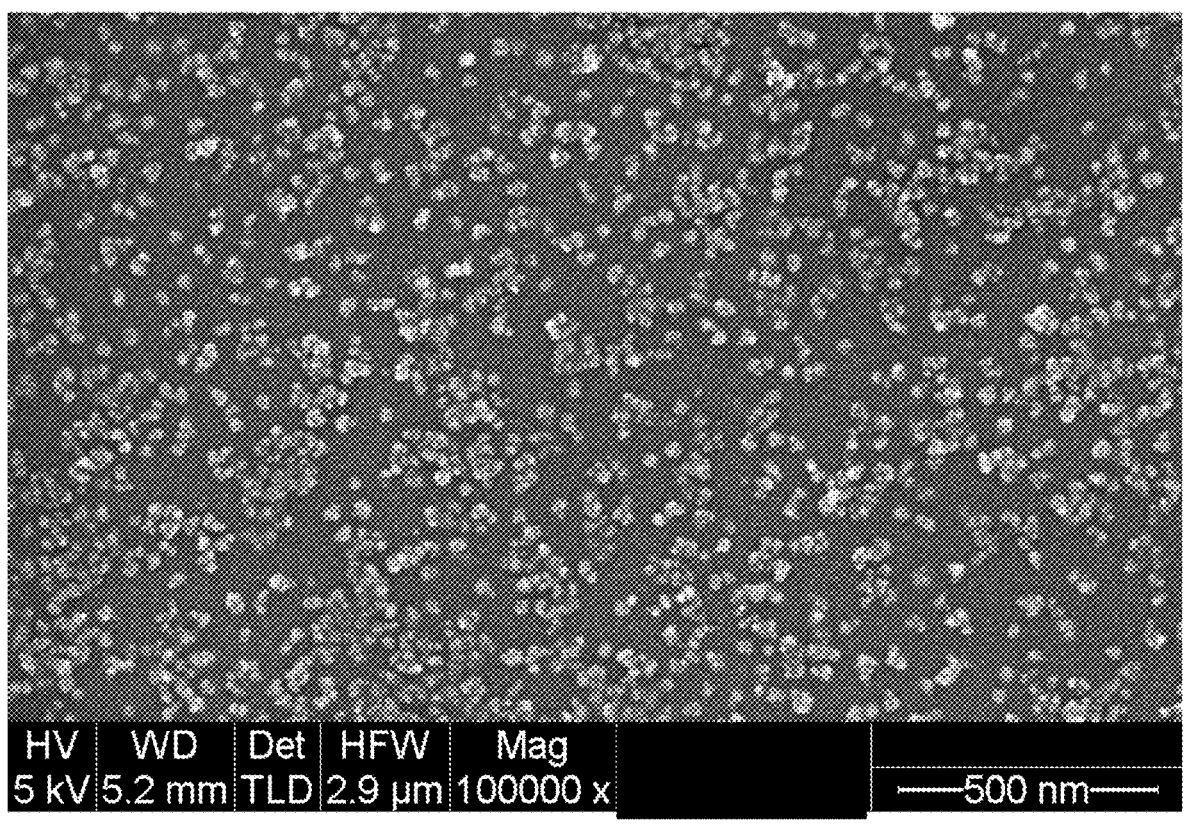
FIG. 5 shows an SEM image of magnetic nanotags.

FIG. 5 shows an SEM image of magnetic nanotags. After the MNT-based analyte quantification, the MNT solution was aspirated and the chips were rinsed twice with de-ionized water to remove salt residues which otherwise would obscure bound MNTs. Chips were then metallized with 1 nm of AuPd by DC sputtering (Hummer V) to enhance image contrast. Images were obtained with an FEI Sirion XL30 scanning electron microscope.

The average diameter of the magnetic nanotags is about 50 nm (commercially available Miltenyi MACS 130-048-102). Upon metallization and inspection in the SEM, these particles appear as roughly 35 nm irregular spheres as shown in FIG. 5, with frequent multi-particle clusters. MACS nanotags appear to contain only a small fraction of magnetic material dispersed throughout a non-magnetic organic matrix to which the functionalization (streptavidin) is bound. In some embodiments, high coverage density was achieved by applying MACS stock solution to a test chip that had been functionalized with biotinylated bovine serum albumin (BSA).

Figure 6:
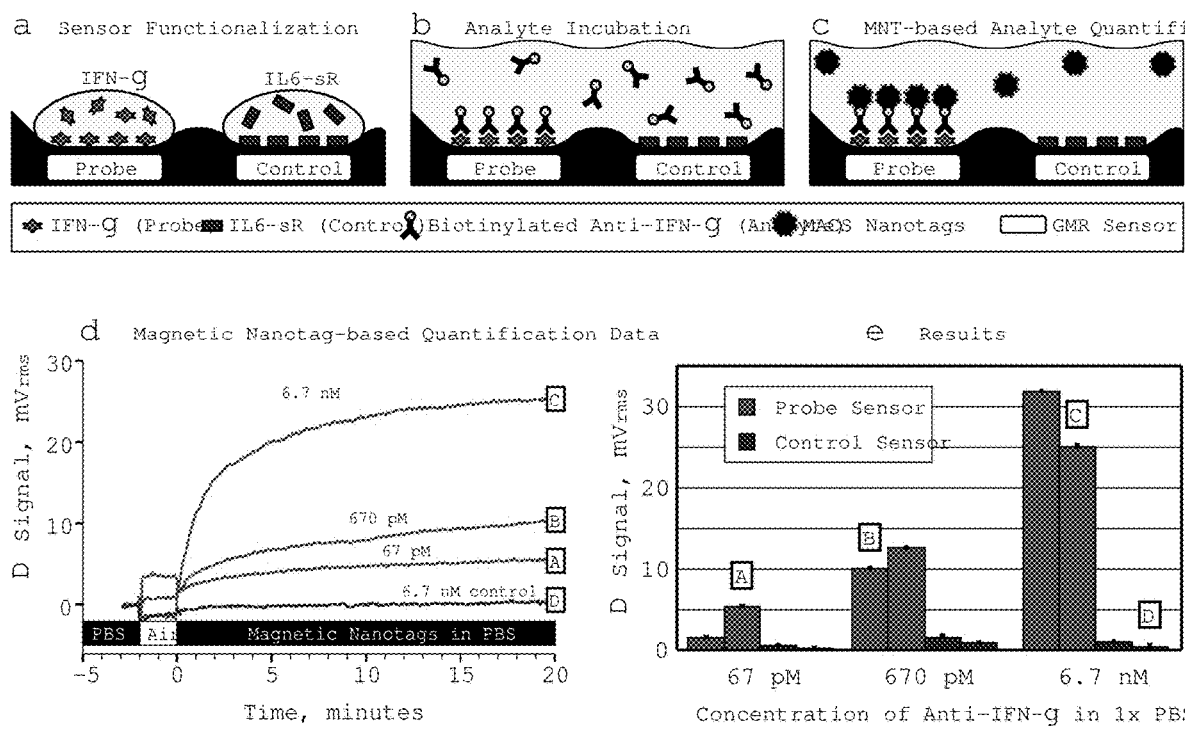
FIG. 6 shows a schematic of a direct binding anti-IFN-γ assay in PBS.

FIG. 6 shows a schematic of a direct binding anti-IFN-γ assay in PBS. In this assay, the analyte is biotinylated anti-IFN-γ, which is captured by IFN-γ functionalized sensors and quantified with streptavidin-coated magnetic nanotags. In some cases, these chips exhibit a reversible signal baseline shift during wet-dry transitions, as can be seen in FIG. 6d from time −2<t<0 minutes. In certain embodiments, the reversible baseline shift can be reduced through passivation, as described above.

In FIG. 6a, probe sensors were functionalized with a 1 µL droplet of IFN-γ, 100 µg/mL in PBS buffer, for 30 minutes at 4° C. Control sensors were functionalized with a 1 µL droplet of IL6-sR, 100 µg/mL in PBS buffer. The functionalized chip was then rinsed with a 1% BSA in 1×PBS buffer solution to block non-specific adsorption sites.

In FIG. 6b, the chip well was filled with 100 µL of analyte, e.g. biotinylated anti-IFN-γ 670 pM (100 ng/mL) in PBS buffer. The analyte was incubated in the entire well of the chips for 1.5 hours at 30° C. The chips were then rinsed with 0.1% BSA in TPBS and transferred to the measuring station for subsequent analyte quantification.

In FIG. 6c, the chip well was filled with 100 µL of Miltenyi MACS stock solution, and the developing MNT binding signal was recorded (see FIG. 6d). The MNT binding signals after 20 minutes of incubation were taken as a measure of analyte concentration (see FIG. 6e). The small error bars indicate the electrical noise of the measurement, which was much smaller than the variance of signals from identically functionalized sensors in this experiment.

Figure 7:
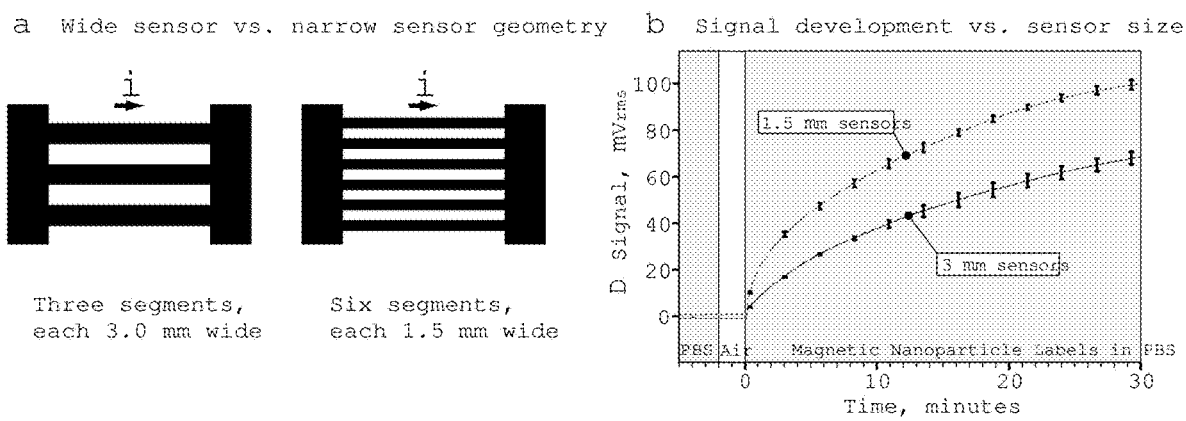
FIG. 7 shows a test of sensor geometry and its effect on sensitivity.

FIG. 7 shows a test of sensor geometry and its effect on sensitivity. FIG. 7 illustrates the evaluation of the effect of sensor segment width while keeping other parameters of the sensors the same. FIG. 7a shows a schematic illustration of simplified sensors with either a wide geometry or a narrow geometry. The schematic illustration on the left of FIG. 7a shows a wide sensor with three segments, each 3 µm wide. The schematic illustration on the right of FIG. 7a shows a narrow sensor with six segments, each 1.5 µm wide. Thus, the total sense current i, the resistance, the sensing area, and the sense current density of these two sensors can all be identical.

To ensure identical experimental conditions for both the wide and narrow sensor types, chips were fabricated that carried both sensor variants inside the same reaction well. The entire reaction well was uniformly functionalized with 100 µL of biotinylated BSA, 200 µg/mL, incubated for 30 minutes at room temperature. No analyte was necessary, since the MNTs can bind directly to the biotinylated BSA. The chips were rinsed twice with PBS and transferred to the measuring station for MNT quantification.

The results (see FIG. 7b) indicate that patterning sensors more finely, as shown in the narrow sensor geometry on the right of FIG. 7a, results in better sensitivity. The median curve for each type of sensor is shown (N=4 curves for each sensor type), with the error bars indicating ±1 standard deviation (see FIG. 7b). The signal from the 1.5 µm sensors was consistently stronger than that from the 3.0 µm sensors (see FIG. 7b). The results show that using more finely patterned sensors with submicron line widths can facilitate an increase in sensitivity.

Figure 8:
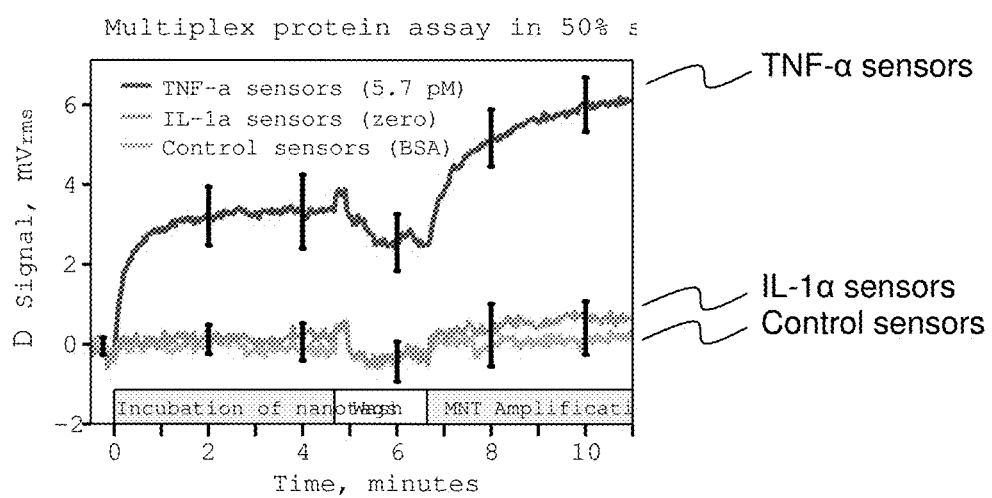
FIG. 8 shows a graph of a multiplex protein assay with nanotag amplification.

FIG. 8 shows a graph of a multiplex protein assay with nanotag amplification, which shows the effect of an optional magnetic nanotag (MNT) amplification step in a multiplex assay. A chip was functionalized with two probes (anti-TNF-α and anti-IL-1α) and one control (BSA), and the applied sample contained 5.7 pM of TNF-α in PBS. The initial MNT-based analyte quantification was performed from 0<t<4.5 minutes. From 4.5<t<6.5 minutes, the chip was first washed, then briefly incubated with biotinylated linker molecules, which attached to the already adsorbed streptavidin-coated MNTs. The already adsorbed MNTs were thus able to capture additional MNTs. A second charge of MNTs was then incubated from t>6.5 minutes. As can be seen from the TNF-α sensors, additional MNTs were captured and a second binding curve was observed, which leveled off at almost twice the signal level of the original MNT binding curve.

III. Reverse Phase

Figure 9:
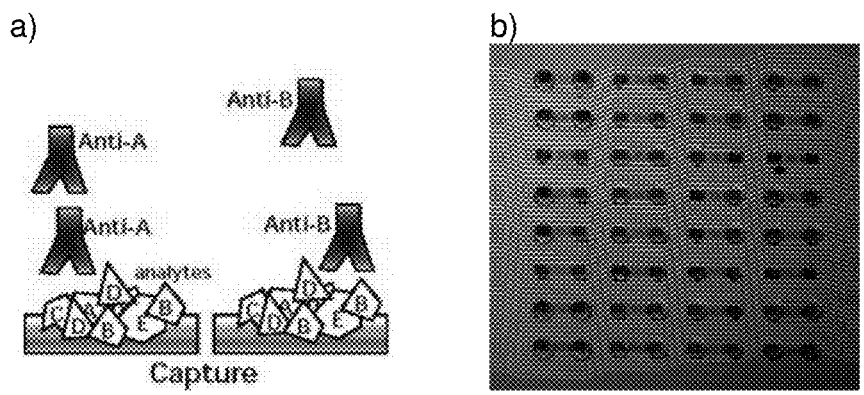
FIG. 9 shows a schematic and image of a reverse phase assay chip.
Figure 10:
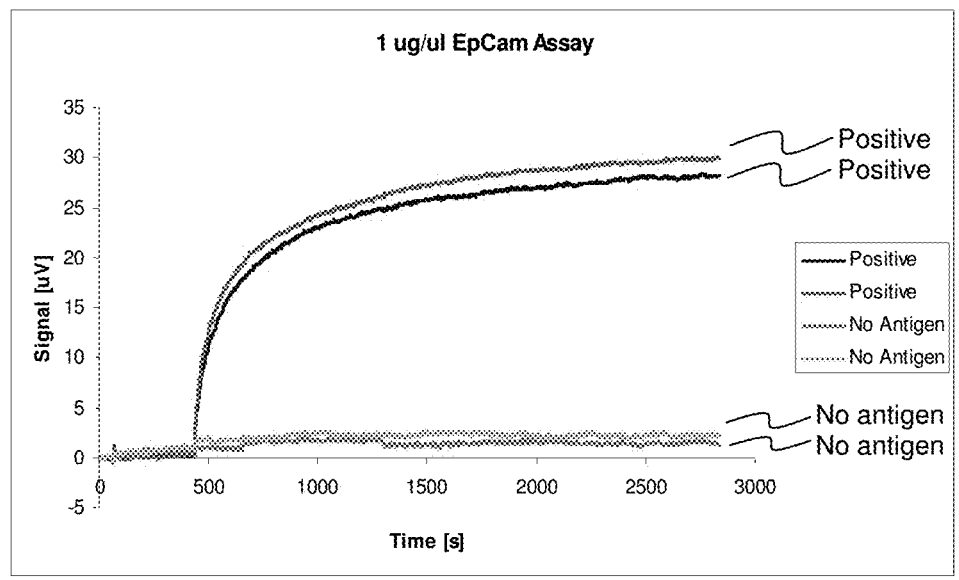
FIG. 10 shows magnetic signals of positive and control sensors versus time in a reverse phase protein detection experiment.

In reverse phase protein (PRP) microarrays, samples from different patients are spotted on a chip and then are incubated with detection agents in a high throughput and multiplexed format. Magneto-nano chips spotted with human cell lysate or serum samples were prepared and then incubated with detection agents made up of selected biomarkers to measure human peripheral blood samples (see FIG. 9). A schematic of a reverse phase protein (RPP) chip is shown in FIG. 9a, and FIG. 9b shows an image of 64 samples spotted on a magneto-nano chip. A graph of the results of protein assays detecting spotted EpCam antigens (a cancer biomarker) using magnetic nanotag sensing is shown in FIG. 10.

In one embodiment, samples containing antigen (e.g., EpCam antigen) were spotted on selected sensors (positive sensors), while no antigen was spotted on control sensors on the same chip. Then, the EpCam antibody functionalized MACS nanoparticle solution was applied to the chip, and the magnetic signals from the sensors were recorded in real time (see FIG. 10), where MACS solution was applied slightly before time t=500 seconds. By fitting the magnetic signal versus time curve, kinetic constants between EpCam antibody and antigen can be extracted. If the solution is diluted at a certain time point, e.g., t=2500 second, desorption of EpCam antibody from antigen occurs, and the off-rate can be extracted by fitting the magnetic signal versus time curve (data not shown).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A magnetic sensor device comprising:
   an analyte specific probe displaying magnetic sensor which displays a probe that specifically binds to an analyte on a surface thereof; and
   a processor configured to obtain a real-time signal comprising a continuous set of data points obtained continuously over a period of time from said magnetic sensor as a magnetically labeled sample is contacted with the magnetic sensor without removing nonspecific magnetic labels from the surface of the magnetic sensor to determine whether said analyte is present in a sample based on the real-time signal.

2. The magnetic sensor device according to claim 1, wherein said magnetic sensor comprises a passivation layer.

3. The magnetic sensor device according to claim 1, wherein said sensor is a spin valve sensor.

4. The magnetic sensor device according to claim 1, wherein said sensor is a magnetic tunnel junction sensor.

5. A system comprising:
   a magnetic sensor device comprising:
      (60) an array of magnetic sensors comprising two or more analyte specific probe displaying magnetic sensors which each display a probe that specifically binds to an analyte on a surface thereof; and
      (ii) a processor configured to obtain a real-time signal comprising a continuous set of data points obtained continuously over a period of time from said magnetic sensor device as a magnetically labeled sample is contacted with the array of magnetic sensors without removing nonspecific magnetic labels from the surface of the magnetic sensors to determine whether said analyte is present in a sample based on the real-time signal.

6. The system according to claim 5, wherein said magnetic sensor comprises a passivation layer.

7. The system according to claim 5, wherein said sensor is a spin valve sensor.

8. The system according to claim 5, wherein said sensor is a magnetic tunnel junction sensor.

9. The system according to claim 5, wherein said system further comprises a magnetic label.

10. A kit comprising:
    (a) the magnetic sensor device according to claim 1; and
    (b) a magnetic label.

11. The kit according to claim 10, wherein said magnetic sensor comprises a passivation layer.

12. The kit according to claim 10, wherein said sensor is a spin valve sensor.

13. The kit according to claim 10, wherein said sensor is a magnetic tunnel junction sensor.

14. The kit according to claim 10, wherein said magnetic label is a colloidal magnetic nanoparticle.

15. The magnetic sensor device according to claim 1, wherein the processor is configured to quantify the analyte based on the real-time signal.

16. The magnetic sensor device according to claim 1, wherein the processor is configured to calculate a slope of the continuous set of data points to determine whether the analyte is present in the sample.

17. The magnetic sensor device according to claim 5, wherein the processor is configured to quantify the analyte based on the slope.

18. The magnetic sensor device according to claim 1, wherein the processor is configured to determine magnetically labeled analyte binding kinetics based on the real-time signal.

19. The system according to claim 5, wherein the array comprises two or more magnetic sensors.

20. The system according to claim 5, wherein the array comprises 10 or more magnetic sensors.

21. The system according to claim 5, wherein the array comprises 20 or more magnetic sensors.

22. The system according to claim 5, wherein the array comprises 50 or more magnetic sensors.

23. The system according to claim 5, wherein the array comprises 100 or more magnetic sensors.

24. The system according to claim 5, wherein two or more of the magnetic sensors in the array are configured to detect distinct analytes.

25. The system according to claim 5, wherein each magnetic sensor is provided in a reaction well.

26. The system according to claim 5, wherein the array of magnetic sensors is provided in a reaction well.

27. The system according to claim 5, wherein the magnetic sensor device comprises two or more arrays of magnetic sensors, and each array is provided in a reaction well.

28. The system according to claim 9, wherein the magnetic label is a colloidal magnetic nanoparticle.

29. The system according to claim 5, wherein the array comprises a control sensor.

30. The magnetic sensor device according to claim 2, wherein said passivation layer has a thickness of about 30 nm or less.

31. The system according to claim 6, wherein said passivation layer has a thickness of about 30 nm or less.

32. The kit according to claim 11, wherein said passivation layer has a thickness of about 30 nm or less.

* * * * *